United States Patent [19]
Mears

[11] Patent Number: 6,136,009
[45] Date of Patent: Oct. 24, 2000

[54] LIGATING BAND DISPENSER

[75] Inventor: Eric L. Mears, Duluth, Ga.

[73] Assignee: Ensurg, Inc., Norcross, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 09/073,511

[22] Filed: May 6, 1998

[51] Int. Cl.[7] .................................................. A61B 17/10
[52] U.S. Cl. ............................................................ 606/140
[58] Field of Search .................................... 606/140, 139, 606/141, 165, 135

[56] References Cited

U.S. PATENT DOCUMENTS

| | | |
|---|---|---|
| 3,760,810 | 9/1973 | Van Hoorn . |
| 3,911,923 | 10/1975 | Yoon . |
| 4,226,239 | 10/1980 | Polk et al. . |
| 4,257,419 | 3/1981 | Göltner et al. . |
| 4,990,152 | 2/1991 | Yoon ...................... 606/140 |
| 5,207,690 | 5/1993 | Rohrabacher et al. .......... 606/135 |
| 5,224,497 | 7/1993 | Ehlers ..................... 128/898 |
| 5,269,789 | 12/1993 | Chin et al. ................ 606/140 |
| 5,320,630 | 6/1994 | Ahmed ..................... 606/140 |
| 5,356,416 | 10/1994 | Chu et al. ................. 606/140 |
| 5,398,844 | 3/1995 | Zaslavsky et al. ............ 221/208 |
| 5,462,559 | 10/1995 | Ahmed ..................... 606/140 |
| 5,507,797 | 4/1996 | Suzuki et al. .............. 606/140 |
| 5,569,268 | 10/1996 | Hosoda .................... 606/140 |
| 5,624,453 | 4/1997 | Ahmed ..................... 606/140 |
| 5,681,328 | 10/1997 | Lamport et al. ............. 606/140 |
| 5,697,940 | 12/1997 | Chu et al. ................. 606/140 |
| 5,735,861 | 4/1998 | Peifer et al. ............... 606/139 |
| 5,857,585 | 1/1999 | Tolkoff et al. ............. 606/140 X |

FOREIGN PATENT DOCUMENTS

| | | |
|---|---|---|
| 0679368A1 | 11/1995 | European Pat. Off. . |
| WO 95/12355 | 5/1995 | WIPO . |
| WO 96/19145 | 6/1996 | WIPO . |

OTHER PUBLICATIONS

Directions for Use Brochure for Speedband™ Multiple Band Ligator, Microvasive Boston Scientific Corporation, pp. 1–8, 1995.

Primary Examiner—Michael Buiz
Assistant Examiner—Vikki Trinh
Attorney, Agent, or Firm—Sidley & Austin

[57] ABSTRACT

A ligating band dispenser has a first sleeve, to store one or more ligating bands, and a second member, which at least partially extends about and is movable relative to the first sleeve. The second sleeve is capable of engaging and moving a distal-most ligating band positioned on the first sleeve from an initial storage position to a dispensing position, irrespective of other ligating bands which may be stored thereon.

35 Claims, 7 Drawing Sheets

LIGATING BAND DISPENSER

FIELD OF THE INVENTION

The present invention relates to a ligating band dispenser, and in particular, to a ligating band dispenser which can sequentially dispense one of a plurality of ligating bands.

BACKGROUND OF THE INVENTION

Ligation is a medical procedure in which an elastic ligating band, for example, is placed about tissue to prevent fluid flow therethrough. Where a ligating band is placed about, for example, a ballooning varix, polyp, hemorrhoid, or pre-cancerous lesion, a contracted ligating band induces fusion and healing in the base tissue and subjects the ligated tissue to necrosis. The necrotic tissue eventually separates from the surrounding tissue and passes into the human system. Alternatively, ligation may also be used for purposes of sterilization, wherein a ligating band may be placed over a folded loop portion of a Fallopian tube or a vas deferens to prevent the passage of internal reproductive fluids.

Means for delivering ligating bands, or ligating band dispensers, take various forms. One such form is a dedicated ligating band dispenser instrument which has a dispensing portion at a distal end, an actuating mechanism at a proximal end, and a typically rigid shaft therebetween. These instruments are useful for ligating tissue in which the user has access to the tissue to be ligated, e.g., tissue exposed through an invasive surgical procedure.

In contrast, ligating band dispensers may be positioned on the distal tip of an endoscope or a laparoscope. An endoscope is a conventional medical device used for viewing, exploring, and delivering therapies to internal regions of a patient. A laparoscope is a specialized endoscope for viewing a patient's peritoneal cavity. Unlike dedicated ligating band dispensing instruments, an endoscope allows minimally invasive intrusion into a patient.

Figures 1, 2, 3:
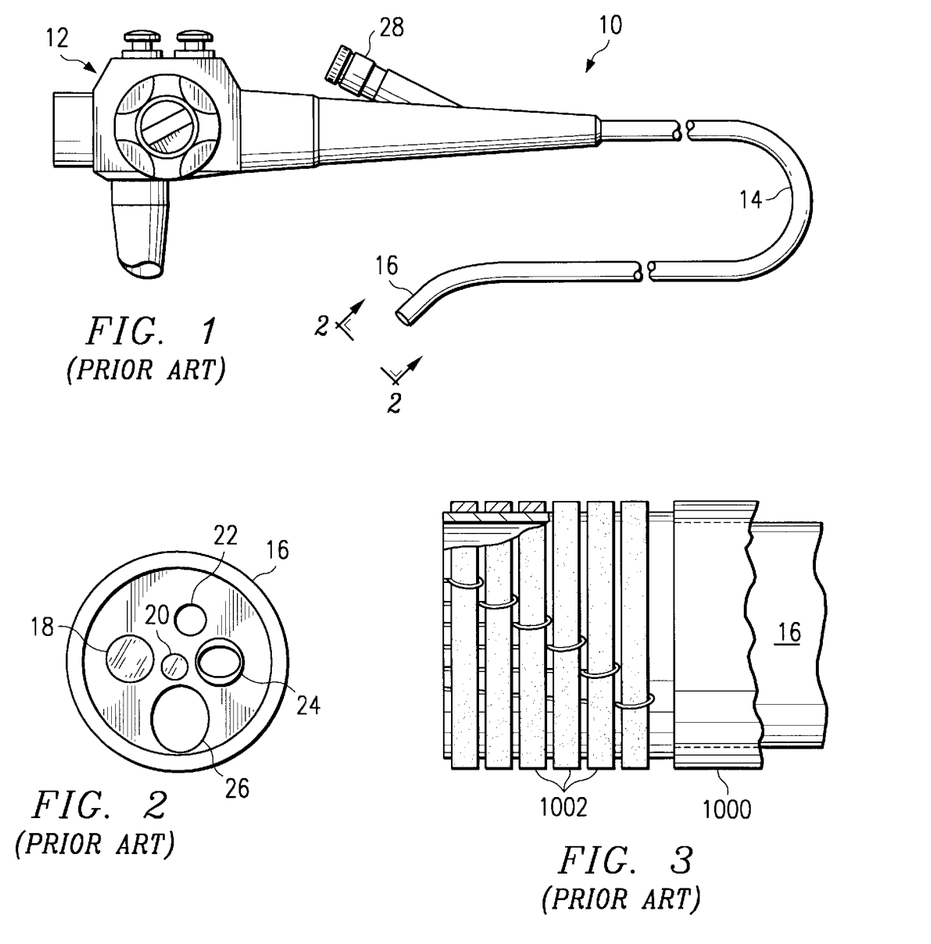
FIG. 1 illustrates a conventional endoscope device.
FIG. 2 is a view along line 2—2 of the insertion tip of the endoscope device of FIG. 1.
FIG. 3 illustrates a conventional ligating band dispenser.

FIGS. 1 and 2 illustrate a conventional endoscope. Endoscope 10 has a control portion 12 and a insertion portion 14 terminating at insertion tip 16. Insertion portion 14 is of such a length to permit access to internal regions of a patient.

FIG. 2 illustrates the face of insertion tip 16. A number of channels extend from the control portion 12 to the insertion tip 16, where the channels terminate in functional outlets 18–26. For the purposes of this example, outlet 18 is a light source; outlet 20 is a wide-field image sensing device, which transmits a video or fiber optic signal to a coupled monitor or eyepiece (not shown) at control portion 12; outlet 22 delivers a stream of water or air for clearing the image receiving device or flushing an internal bodily region; and outlet 24 is an outlet to a working (or biopsy) channel. Inlet 28 of the working channel can be coupled to a suction device or a lavage fluid source (not shown) or can receive various medical instrumentation (not shown) for passage through the working channel and outlet 24. Optional outlet 26, for larger diameter endoscopes, is an outlet for a second working channel. A second working channel allows additional operations in a manner consistent with the working channel described above.

Endoscope ligating band dispensers are fixedly mounted about and protrude from insertion tip 16 of a hosting endoscope, wherein such dispensers carry one or more expanded ligating bands about their outer diameter. Projecting from insertion tip 16, conventional dispensers inherently narrow the field of view of the image sensing device of outlet 20. In an effort to improve such impairment, some conventional devices are fabricated from a transparent material. While such material may facilitate the outward passage of light from outlet 18, such material does not practically improve the field of view for the wide-field image sensing device. Specifically, the use of transparent material commonly induces distortion about the periphery of a displayed image. Distortion is a product of both the curvature of the dispenser and the accumulation of bodily fluids about the outer surface of the dispenser. Ligating bands stored on the outer diameter of these dispensers further obstruct the field of view through the dispenser material.

Conventional endoscope ligating band dispensers commonly employ dispensing mechanisms which unnecessarily complicate a ligating procedure. Two examples of conventional mechanisms include a dispenser having a plurality of draw strings 1002 which are individually coupled to each of the stored ligating bands 1000 (FIG. 3) and a dispenser having a mechanically actuated housing which engages and requires movement of all stored ligating bands 1000 for each dispensing operation (FIG. 4).

In reference to FIG. 3, draw strings 1002 extend from each ligating band 1000 and around the distal end of the dispenser before extending proximally through the work channel of a receiving endoscope 10. Application of a proximally-directed force to a single draw string 1002 effects distal movement and dispensing of a coupled ligating band 1000. Understandably, during a procedure, a user must be keenly aware of which draw sting 1002 is being controlled to prevent the inadvertent dispensing of ligating bands 1000.

Figure 4:
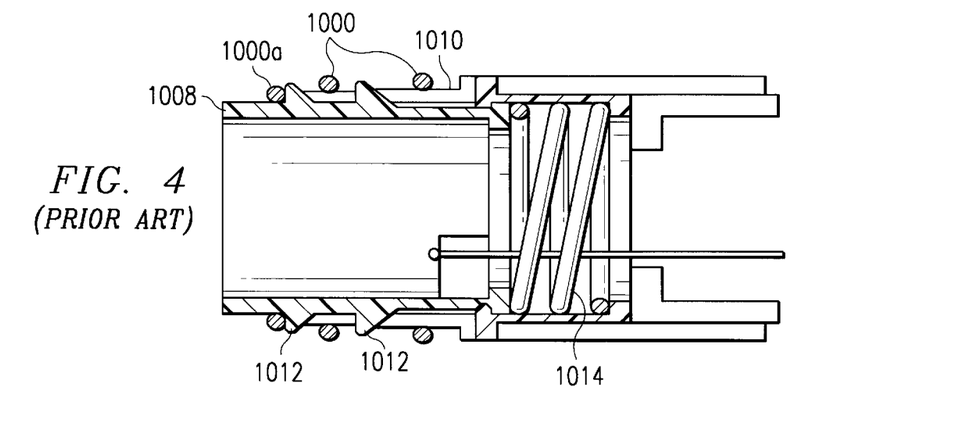
FIG. 4 illustrates a conventional ligating band dispenser.

Referring to FIG. 4, another conventional dispenser example includes a mechanically actuated housing having a movable inner element 1008 and a fixed outer element 1010. Outer element 1010 carries a plurality of expanded ligating bands 1000, excepting the distal-most ligating band 1000a, which is carried by inner element 1008. For dispensing ligating band 1000a, element 1008 is drawn proximally, causing the distal-most ligating band 1000a to be released when inner element 1008 is pulled within outer element 1010. During such movement, the remaining ligating bands 1000 are displaced by shoulders 1012 so that when inner element 1008 returns distally, ligating bands 1000 are distally advanced. These conventional mechanisms require additional moving structure (for example, a spring 1014 to bias inner sleeve 1008 in a distal direction) which can increase the complexity, cost, and size of such devices. Additionally, attempting to maintain the dispenser at a reasonable length, the inclusion of elements such as shoulders 1012 may limit the number of ligating bands which may be stored.

Of further consideration, the dispenser of FIG. 4 can require an applied dispensing force having a magnitude sufficient to not only dispense a single ligating band but also distally displace the remaining stored ligating bands in preparation for a next ligation. As the number of stored ligating bands increase, the force necessary to move the ligating bands as a group also increases. Consequently, a user may experience some level of awkwardness during a procedure due to the force which may be necessary to dispense one or more ligating bands.

Conventional dispensers increase the length of insertion tip 16. A ligating band dispenser-equipped endoscope is commonly used within a hollow body cavity, for example, an esophagus. Insertion tip 16 must assume almost a 90° bend with respect to the longitudinal axis of the insertion portion 14 to obtain a clear view normal to the inner surface of an esophagus. The additional length of the ligating band dispenser from insertion tip 16 can significantly restrict the motion and flexibility of insertion tip 16 within a hollow body cavity. Accordingly, the added length, coupled with the severely restricted peripheral view, makes the presence of conventional ligating band dispensers an operational liability during the exploration and placement phases of ligation procedures.

SUMMARY OF THE INVENTION

The present invention is directed to a ligation band dispenser. According to one aspect of the present invention, a ligating band dispenser includes a first member and a second member. The first member is characterized by a surface to support two or more ligating bands, and the second member is adapted to engage and continuously move each ligating band from an initial stored position to a release position. In one embodiment of this aspect, the second member extends at least partially about and is movable relative to the first member. The second member may also include at least one capturing element to facilitate the engagement of each ligating band.

According to another aspect of the present invention, a ligating band dispenser is disclosed with a first member having both a surface to support one or more ligating bands and a longitudinal axis, and a second member having at least one capturing element to individually engage and move only a distal-most ligating band to a release position. The second member is slidably received by and at least partially extends about the first member. Movement of the second sleeve effects a displacement of the second member in a direction parallel to the longitudinal axis of the first member.

According to another aspect of the present invention, a ligating band dispenser has a first hollow member adapted to carry one or more expanded ligating bands; a second member; and an actuating mechanism coupled to the second member to selectively move the second member relative to the first member. The second member at least partially extends about the first member and is movable relative to the first member to effect a displacement in a direction parallel to the longitudinal axis of the first member. The second member has one or more inwardly-biased members to engage and move a ligating band to a release position for a band dispensing operation.

For a ligating band dispensing operation, a dispenser in accordance with the present invention is fixed to a distal end of an insertion portion of a receiving endoscope. Once the ligating tissue has drawn into a conventional ligating position within the dispenser, the second member is moved proximally until the one or more inwardly-based members are positioned proximate of a distal-most expanded ligating band carried on the first member. The one or more inwardly-biased members displace outwardly about the distal-most expanded ligating band through a portion of the proximal movement of the second member. Subsequently, the second member is moved distally to move the engaged distal-most expanded ligating band beyond a distal end of the first member for dispensing.

An object of the present invention is to provide a ligating band dispensing device which accurately and consistently dispenses a single ligating band per dispensing operation.

Another object of the present invention is to provide a ligating band dispensing device which stores a large number of bands with no operational disadvantages.

Another object of the present invention is to provide a ligating band dispensing device which stores at least one ligating band, prior to selection for dispensing, free of positional biasing.

Another object of the present invention is to provide a ligating band dispensing device which protects stored bands from premature release during insertion and exploration.

Another object of the present invention is to provide a ligating band dispensing device constructed to maximize patient comfort, minimize complexity, whether operational or in design, and maintain single band-delivery accuracy.

Another object of the present invention is to provide a control mechanism to effect the indirect and sequential selection and dispensing of a single ligating band from a plurality of ligating bands.

Another object of the present invention is to provide a ligating band dispensing device which may assume a first position for an increased field of view for an image sensing device of a hosting endoscope and may assume a second position for dispensing a ligating band.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Figure 5A:
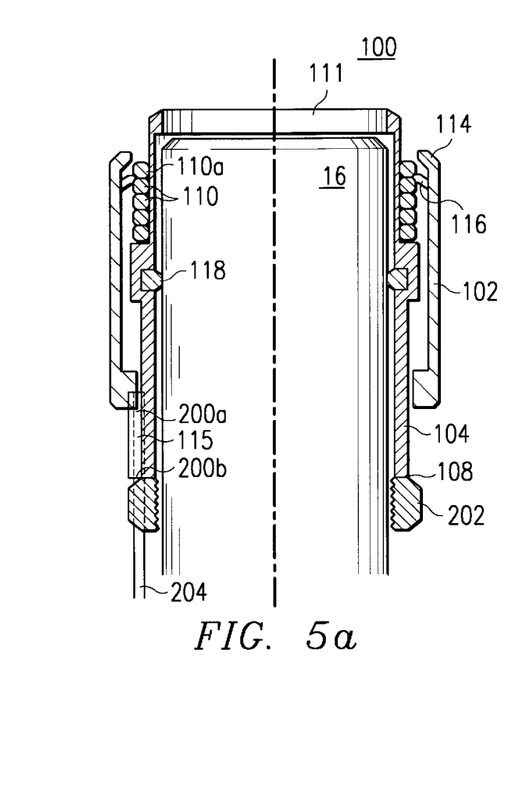
FIGS. 5a through 5c is a partial, sectional view of a movable ligating band dispenser of a first embodiment.
Figure 5B:
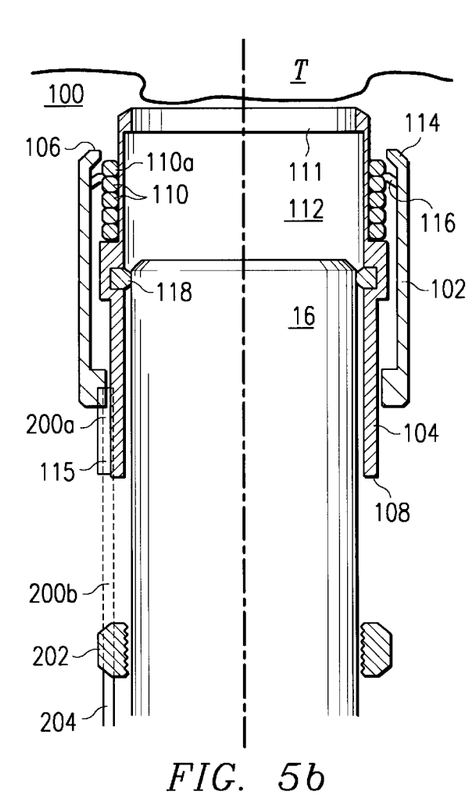
Figure 5C:
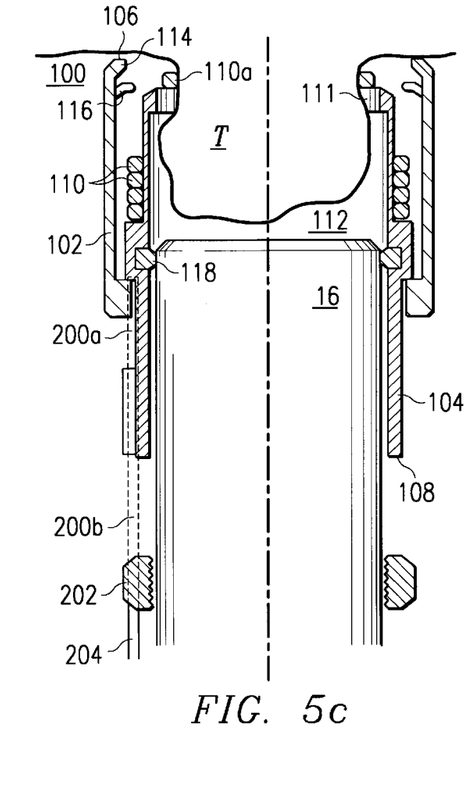

FIGS. 5a through 5c illustrate one embodiment of a movable dispenser 100. Dispenser 100 includes dispensing member (an outer sleeve) 102 slidably received on sleeve 104 (an inner sleeve), sleeve 104 being adapted to fit about insertion tip 16 of a hosting endoscope 10. Both dispensing member 102 and sleeve 104 have a cross-sectional shape consistent with the outer shape of insertion tip 16 of an endoscope 10, wherein such shape is typically circular in nature. Dispensing member 102 and sleeve 104 are constructed of a medical grade material suitable for exposure to a human system and which display low friction characteristics when in contact. Moreover, at least dispensing member 102 may be constructed of a transparent or translucent material to facilitate the passage of light when in an extended position (FIGS. 5b and 5c).

Referring to FIGS. 5a through 5c, dispenser 100 is generally cylindrical in shape and has a distal end 106 and a proximal end 108. The distal end of sleeve 104 defines opening 111 which has a diameter substantially consistent with the face diameter of insertion tip 16. Opening 111 allows use of the functional outlets 18–26 (FIG. 2) of the hosting endoscope, for example, transmission of light, passage of instrumentation, receipt of visual imaging, and the like. Sleeve 104 further includes a region, just proximal to its distal end, which carries at least one expanded ligating band 110. Preferably, sleeve 104 carries a plurality of expanded ligating bands 110.

Dispensing member 102 has a fixed shoulder 114 and at least one inwardly-biased, spring finger 116. Preferably, dispensing member 102 includes two or more spring fingers 116. The distance between shoulder 114 and the aligned spring fingers 116 is approximately equal to the diameter of a single ligating band 110. To limit undesired rotation of dispensing member 102, dispensing member 102 may include a recess or the like (not shown) along an inner surface to receive a longitudinal protrusion 115 which extends along an outer surface of sleeve 104. Alternatively, protrusion 115 could spiral about sleeve 104 (not shown), to induce a desired rotation, and facilitate a predetermined rate of extension of dispensing member 102 relative to sleeve 104.

Operation of dispenser 100 is illustrated by FIGS. 5a through 5c. FIG. 5a illustrates a first condition in which dispenser 100 is in a retracted position. Once tissue T for ligation is identified, dispenser 100 is extended to a dispensing position (FIG. 5b), thus creating volume 112, substantially defined by an inner surface of sleeve 104, to receive the chosen tissue T. To ready ligating band 110a, dispensing member 102 is drawn proximally until the spring fingers 116 are proximal to the distal-most ligating band 110a (FIG. 5b).

Volume 112 is subjected to a suction to draw tissue T therein (FIG. 5c), or tissue T is physically drawn into volume 112 using forceps (not shown) or the like which are passed through the work channel of endoscope 10 to the distal end 16 of dispenser 100. For dispensing, dispensing member 102, and thus ligating band 110a, are caused to move distally. When dispensing member 102 nears full extension, ligating band 110a is released. Following dispensing of the required number of ligating bands 110, dispenser 100 may again be retracted, and the sequence repeated, if desired.

In a retracted position, it is preferred that the distal end 106 of ligating band dispenser 100 be substantially aligned with the distal end of insertion tip 16. However, because certain ligating band dispensing mechanisms and structure (i.e., those formed substantially along an inner periphery of dispenser 100 within chamber 112) may prevent this preferred position, a "retracted position" means a ligating band dispenser position which facilitates an improved field of view over a fully extended (or conventional) ligating band dispenser position and/or defines a volume (volume 112) which is insufficient to enable a ligation procedure.

Figure 6:
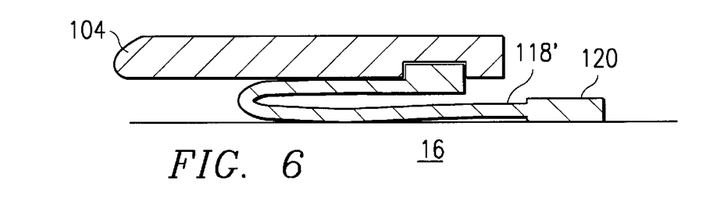
FIG. 6 is a partial, sectional view of a rolling diaphragm seal for an alternative embodiment of at least the movable ligating band dispenser of FIGS. 5a–5c.

As discussed above, a suction may be applied to draw tissue T into volume 112. Necessarily, a seal must be established between the insertion tip 16 of the endoscope 10 and sleeve 102 to efficiently maintain an applied suction. FIGS. 5a–5c show one embodiment of seal 118. More specifically, seal 118 is an o-ring type seal or v-ring, lip-type seal which slidably engages insertion tip 16 throughout the motion of sleeve 104. Seal 118 may also take the form of a rolling diaphragm (FIG. 6). For this embodiment, seal 118' includes a thin membrane coupled to dispensing member 102 and anchored to insertion tip 16. Seal 118' is joined to insertion tip 16 through application of an adhesive or, more preferably, by an integral elastic band 120 which tightly engages endoscope 10. As another alternative, a portion of sleeve 104 at or about proximal end 108 could be constructed of a flexible material which circumferentially extends about insertion tip 16. For this alternative, sleeve 104 can move relative to insertion tip 16 consistent with the above examples; however, when a suction is applied to volume 112 the flexible material is caused to contract about insertion tip 16 to both establish a seal and reduce those forces transmitted to actuating filament 200b due to the tendency of dispenser 100 to retract when the suction is applied.

While the above description sets forth three examples of seal 118, one skilled in the art will appreciate that seal 118 may take any variety of forms. Importantly, however, seal 118 of the present invention maintains a fluid-tight seal when dispenser 100 is at least in an extended position, and at least a portion of seal 118 travels through the extension/retraction motion of dispenser 100.

Figure 7A:
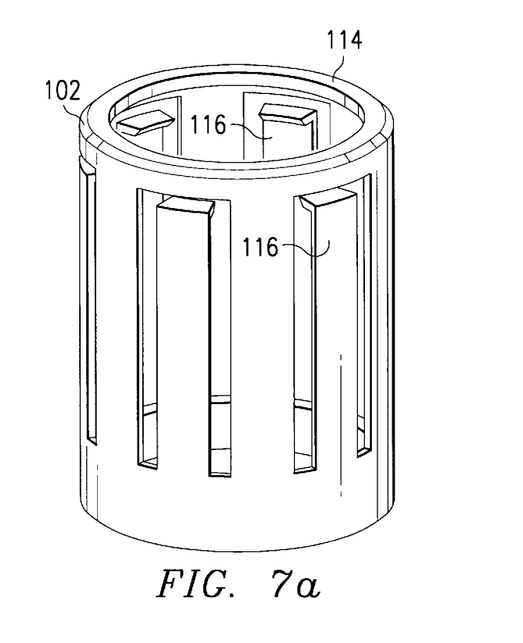
FIG. 7a is a perspective view of the dispensing member of FIGS. 5a–5c.

Dispensing member 102 of FIGS. 5a–5c is also shown in FIG. 7a, wherein dispensing member 102 has a fixed shoulder 114 and a plurality of spring fingers 116. Consistent with the configuration of dispensing member 102 which allows only a single stored ligating band 110 to be engaged/dispensed and which extends at least partially about sleeve 104, alternative embodiments of dispensing member 102 are shown in FIGS. 7b–7i.

Figure 7B:
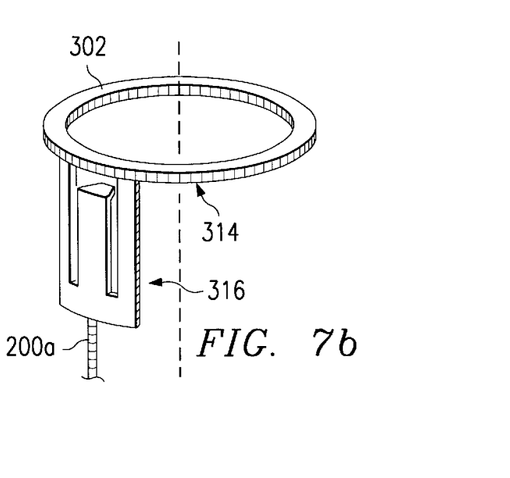
FIGS. 7b and 7c are perspective views of alternative, related embodiments of a dispensing member.
Figure 7C:
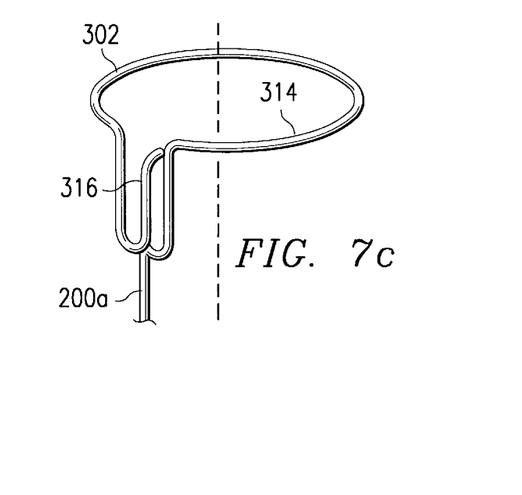

FIG. 7b illustrates dispensing member 302, which is similar in construction and operation to dispensing member 102. Specifically, distal ring 314 and spring finger 316 are analogous to shoulder 114 and spring fingers 116, respectively. Inherent to its physical arrangement, dispensing member 302 does not fully encompass sleeve 104 and stored ligating bands 110 positioned thereon. Moreover, distal ring 314 may be constructed so as not to completely encircle receiving sleeve 104. FIG. 7c shows a like dispensing member formed of metal wire or the like. While FIGS. 7b and 7c illustrate a single spring finger 316, one skilled in the art shall appreciate that additional spring fingers 316 may be included along distal ring 316.

Figures 7D, 7E, 7F, 7G:
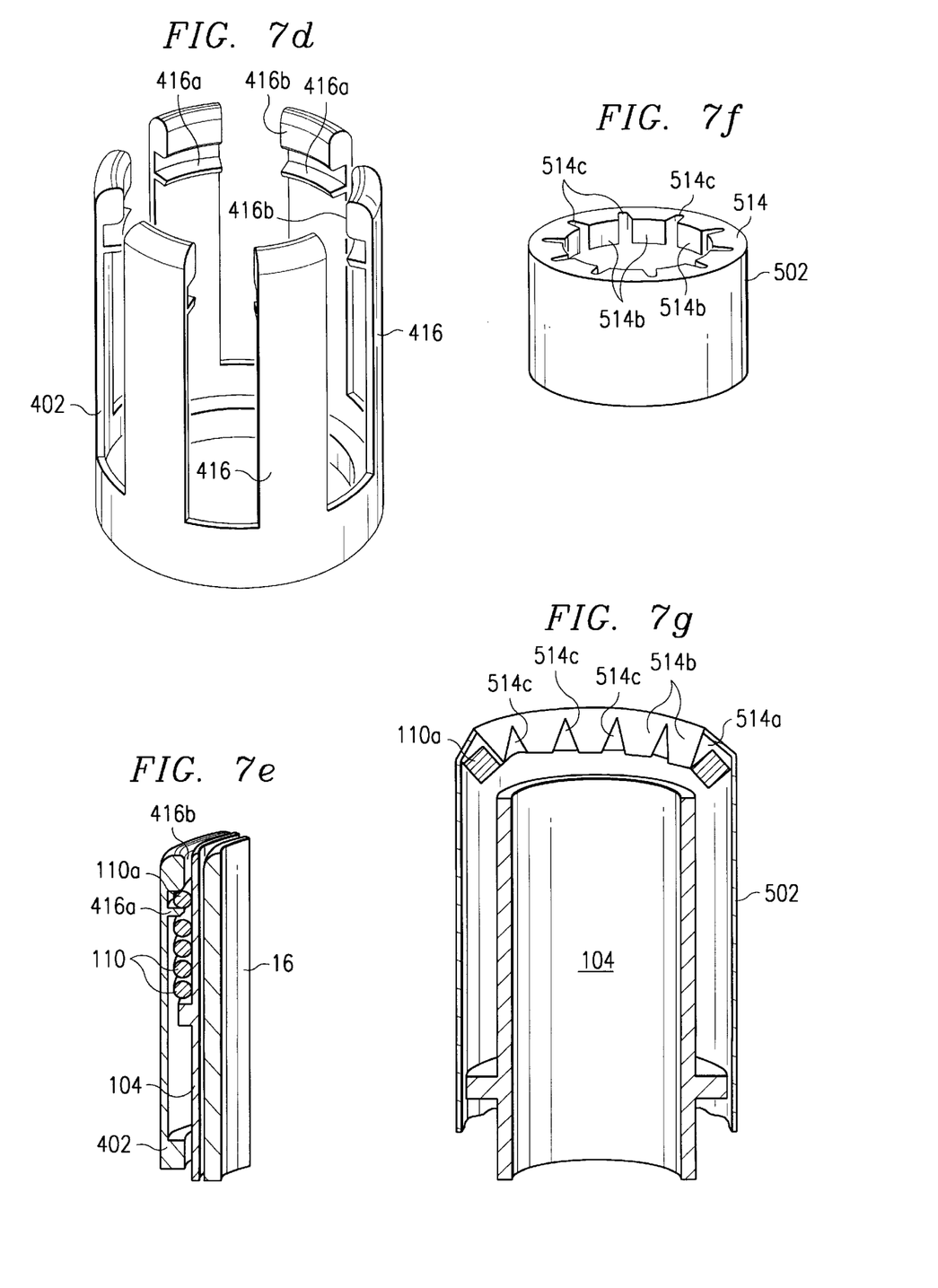
FIG. 7d is a perspective view of another embodiment of a dispensing member.
FIG. 7e is partial, sectional perspective view of the dispensing member of FIG. 7d in an operational position.
FIG. 7f is a perspective view of another embodiment of a dispensing member.
FIG. 7g is a partial, sectional perspective view of the dispensing member of FIG. 7f in an operational position.

FIG. 7d illustrates dispensing member 402 having one or more spring fingers 416 having at least two inwardly directed protrusions 416a, 416b. In a preferred embodiment, protrusion 416a is thin and is capable of fitting between stored ligating bands 110 (FIG. 7e). Protrusion 416b has a width greater than the spacing between ligating bands 110 and is distally positioned from protrusion 416a an amount approximately equal to the width of a ligating band 110. Functionally, dispensing member 402 allows a full range of distal and proximal movement, unlike dispensing member 102 whose proximal movement is limited by contact between shoulder 114 and ligating band 110a (FIG. 5a). As dispensing member 402 is drawn proximally, the flexibility of spring fingers 416 allow protrusion 416a to pass about ligating bands 110. When protrusion 416a is positioned proximal to any ligating band 110 other than ligating band 110a, however, protrusion 416b does not allow protrusion 416a to engage the proximal ligating band 110. FIG. 7e illustrates a "loaded" condition where the distal-most ligating band 110a is positioned between protrusions 416a, 416b.

Another embodiment of a dispensing member is illustrated in FIG. 7f. Dispensing member 502 has ligating band engaging lip 514. When extending along sleeve 104, engaging lip 514 forms c-channel 514a which has a height and a depth sufficient to carry a single ligating band 110a. To load, dispensing member 502 is moved proximally until ligating band supporting surfaces 514b are interposed between sleeve 104 and the distal-most ligating band 110a. For dispensing, dispensing member 502 is moved distally. When dispensing member 502 reaches a dispensing position, band supporting surfaces 514b are unsupported, and slots 514c, which separate supporting surfaces 414b, permit supporting surfaces 514b to flex inwardly under the applied force of the expanded ligating band 110a (FIG. 7g).

Figure 7H:
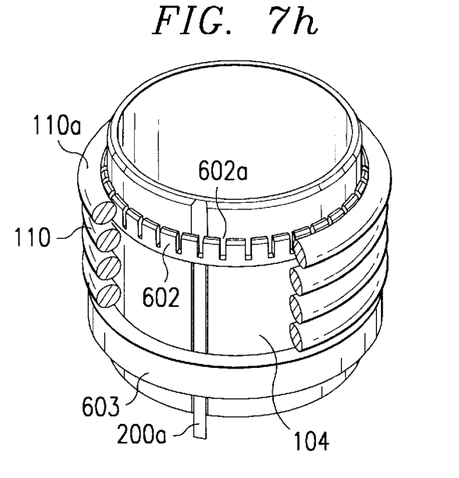
FIGS. 7h and 7i are perspective views of alternative, related embodiments of a dispensing member.
Figure 7I:
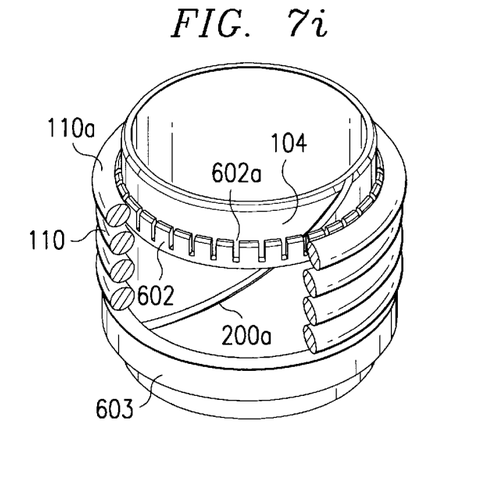

FIG. 7h shows an axially actuated band supporting sleeve 602 having a width substantially equal to the width of a stored ligating band 110a. Supporting sleeve 602 includes a plurality of slots 602a which allow a predefined flexibility to be achieved when supporting sleeve 602 is in a dispensing position. Specifically, when supporting sleeve 602 is at a distal-most position relative to sleeve 104, at least a portion of the supporting sleeve 602 extends beyond, and is not supported by, sleeve 104, thus supporting sleeve 602 assumes an inwardly-directed conical shape to facilitate dispensing of a supported ligating band 110a. Proximal movement of supporting sleeve 602 is limited by stop 603. Supporting sleeve 602 is driven by driving member 200a. To enable movement of supporting sleeve 602 without disturbing other stored ligating bands, driving member 200a preferably passes beneath any stored ligating bands 110 in a recess or the like formed in the outer surface of sleeve 104. FIG. 7i is similar to the embodiment of FIG. 7h; however, supporting sleeve 602 follows a helical path about sleeve 104 to a dispensing position.

Dispenser 100 is extended and retracted using an actuating mechanism. An actuating mechanism in accordance with the present invention includes actuating elements 200, which are coupled between dispenser 100 and controller 150, which will be discussed in greater detail below.

FIGS. 5a–5c illustrate one embodiment of actuating elements 200. Actuating elements 200 are preferably semi-rigid filaments or thin cable (collectively "filaments") formed from stainless steel, nitinol, or the like. For this embodiment, actuating filaments 200 are exterior to and extend along the outer surface of insertion portion 14. Actuating filament 200a is coupled to dispensing member 102 and effects movement of the dispensing member 102, while actuating filament 200b is coupled to sleeve 104 to effect retraction/extension of dispenser 100. In operation, distally-directed forces applied to filaments 200a, 200b cause an extension of dispensing member 102 and sleeve 104, respectively, while a proximally-directed force applied to filaments 200a, 200b cause a retraction of the same. In some instances, certain actuating elements 200 can perform multiple tasks to simplify operations, for example, a distally-directed force applied to actuating filament 200b can effect the extension of both members 102, 104 and, when dispenser 100 is extended, a proximally-directed force applied to actuating filament 200b can effect a retraction of both members 102, 104. While these embodiments of actuating element 200 operate in response to the application of axial forces, actuating elements 200 could include features to effect extension/retraction of dispenser 100 and/or dispensing of ligating bands 110 in response to an applied rotation.

Actuating filaments 200a, 200b pass through grasping ring 202. Preferably, ring 202 is an independent elastic band which is positioned proximal of dispenser 100 and tightly holds to the insertion tip 16. Preferably, filaments 200a, 200b are covered with a load bearing encasement 204, which terminates at and is integral with ring 202. Operatively, ring 202 asserts a force against casing 204 which is at least equal and opposing to any distally-directed forces applied to actuating filaments 200a, 200b. Ring 202 may further include securing means to receive and releasably secure sleeve 104 in a retracted position. If not independent, ring 202 can dually serve as the anchor 120 for the rolling diaphragm seal 118' of FIG. 6. For this embodiment, actuating filaments 200a, 200b may be further secured along the length of the insertion portion 14 with tape, adhesive, additional elastic bands, a spiral wrap of actuating filaments 200a, 200b about insertion portion 14, or the like.

FIGS. 8a–8d illustrate other embodiments and combinations of actuating elements 200. Common to these embodiments, however, actuating elements 200 pass through outlet 24 and extend internally through the work channel of insertion portion 14 to inlet 28.

Figure 8A:
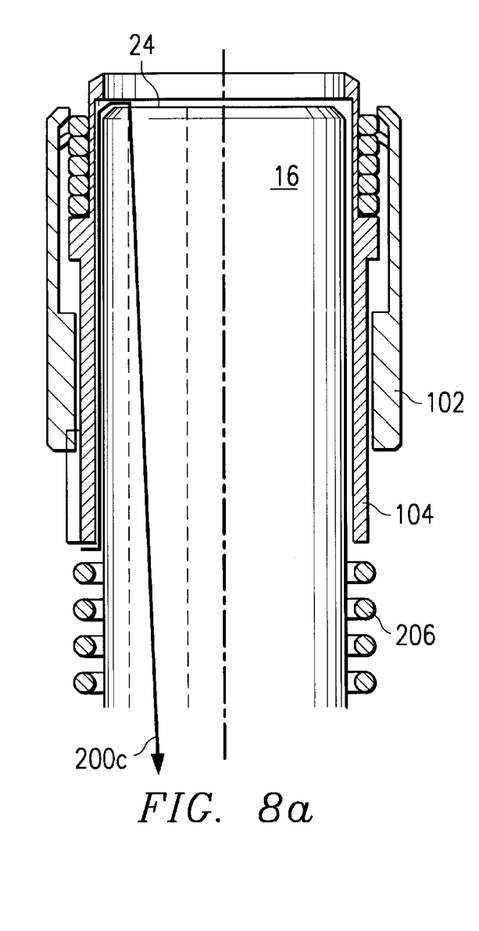
FIGS. 8a and 8b are partial, sectional views of a movable ligating band dispenser of another embodiment.
Figure 8B:
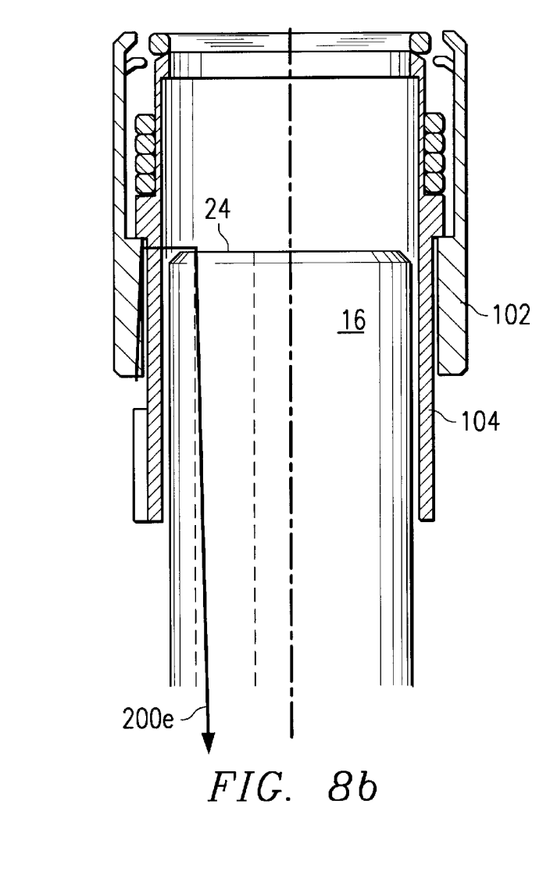

FIG. 8a preferably illustrates dispenser 100 biased proximally by spring 206. Actuating filament 200c is coupled to the proximal end of sleeve 104, and a proximally-directed force applied to filament 200c caused dispenser 100 to be extended. In contrast, FIG. 8b shows a distally-biased dispenser 100 using spring 206. Actuating filament 200c is coupled to the distal end of sleeve 104, and a proximally-directed force applied to filament 200c causes dispenser 100 to be retracted. Rather than a conventional spring, biasing element 206 may assume, for example, an elastic sleeve (not shown) or the like which functions similar to a spring and in a manner described above. For clarity, actuating filaments 200 for dispensing stored ligating bands 110 are not shown in either of these figures.

Figure 8C:
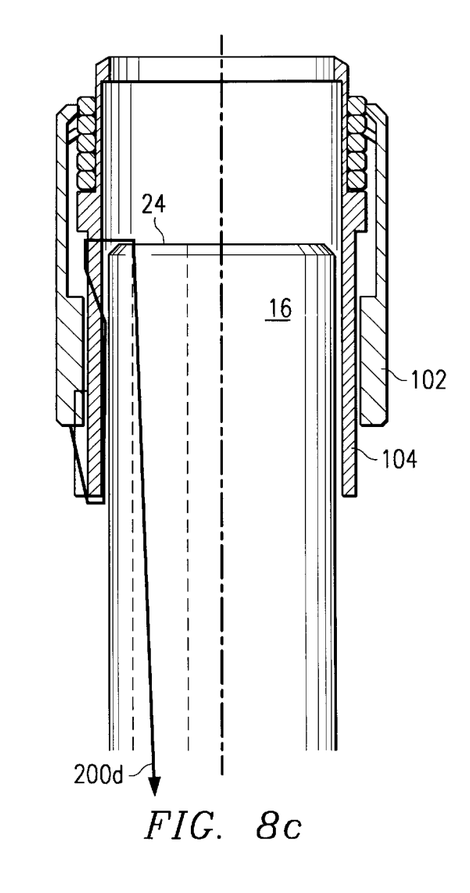
FIG. 8c is a partial, sectional view of a movable ligating band dispenser having an actuating filament.

FIG. 8c illustrates actuating filament 200d to extend sleeve 104 and retract dispensing member 102 to "load" the distal-most ligating band 110a between shoulder 114 and spring fingers 116. Actuating filament 200d is secured at a proximal end of dispensing member 102 and passes around both the proximal end of sleeve 104 and the distal end of insertion tip 16 before entering outlet 24 and the work channel of endoscope 10. Alternatively, if the configurations of either FIG. 8a or FIG. 8b are combined with the configuration illustrated in FIG. 8c, actuating filament 200d is used exclusively for readying a ligating band 110 for dispensing.

Figure 8D:
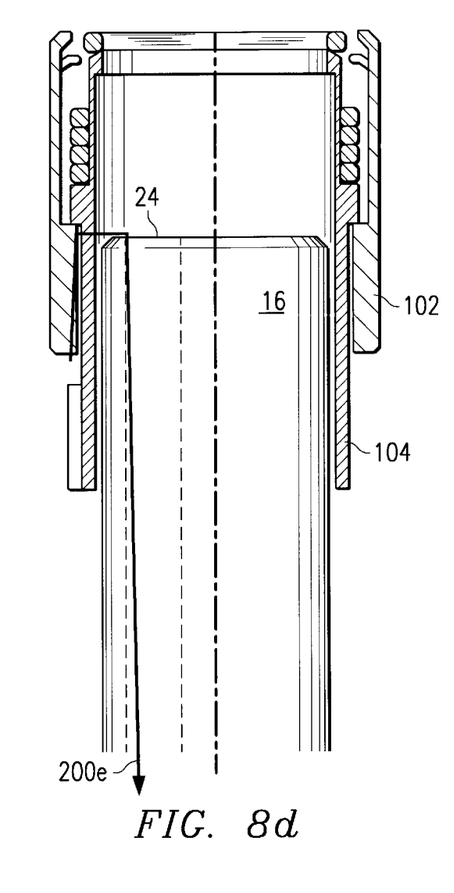
FIG. 8d is a partial, sectional view of a movable ligating band dispenser having an actuating filament.

FIG. 8d illustrates actuating filament 200e which functions to dispense a loaded ligating band 11a. Application of a proximally-directed force to actuating filament 200e causes dispensing member 102 to move distally and dispense ligating band 110a. Actuating filament 200e is secured to the proximal end of dispensing member 102 and passes around the distal end of insertion tip 16 before entering outlet 24 and the work channel extending through endoscope 10.

As actuating filaments 200d, 200e are used to load and dispense each ligating band 110, dispenser 100 of this embodiment will necessarily include both actuating filaments 200d, 200e. Accordingly, actuating filaments 200d, 200e may be independent filaments or portions of a single filament.

While the examples set forth in FIGS. 8a–8d provide specific filament attachment points and other references, one skilled in the art shall appreciate that these attachment points/references are but one set of examples, and that the actuating filaments may be joined at other points of dispenser 100 to effect the movement of dispenser 100 in a manner consistent with the present invention. Moreover, other actuating systems, for example, hydraulic or pneumatic systems (not shown) may also facilitate the extension/retraction of dispenser 100, wherein actuating elements would be fluid tubing (not shown) spanning between a pressurized fluid source and dispenser 100.

Figure 9:
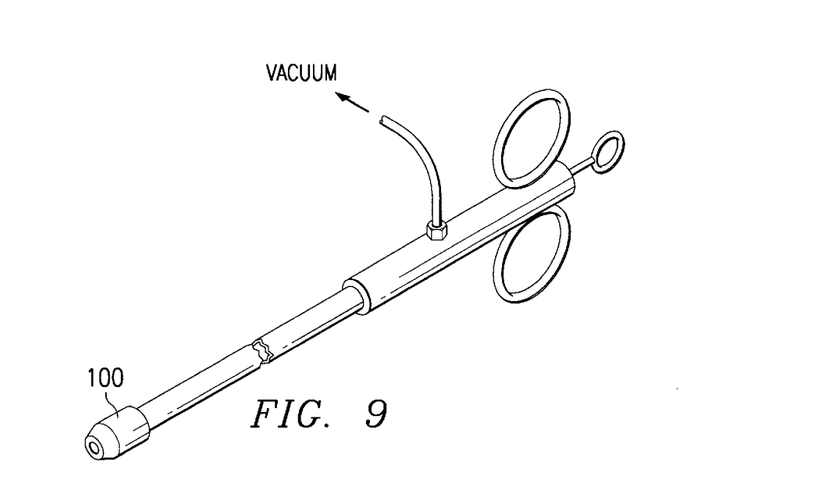
FIG. 9 is a perspective view of a ligating band dispensing instrument having a ligating band dispenser in accordance with the present invention.

Although the above description has been directed to a movable dispenser 100, dispenser 100 can be removably fixed to insertion tip 16 of a receiving endoscope 10 in a manner consistent with conventional ligating band dispensers. Further, dispenser 100 can be fixed to or formed as a part of a dedicated ligating instrument (FIG. 9).

As provided above, actuating elements 200 are coupled between dispenser 100 and controller 150. While actuating elements 200 can be manipulated directly by the user (e.g., by hand), controller 150 enables a user to accurately and selectively control the dispensing of a stored ligating band 110 and/or the movement of dispenser 100. Controller 150 may be rather simple (for example, a filament wrapped-shaft [not shown] having filament portions 200d, 200e extending therefrom, wherein the combined tension on filaments 200d, 200e can effect the extension of dispenser 100 and rotation of the shaft while under tension effects at least the loading and dispensing of ligating band 110a); however, in reference to FIG. 10 controller 150 preferably includes user interface 152, translator 154, dispenser position controller 156, and dispenser controller 158.

Figure 10:
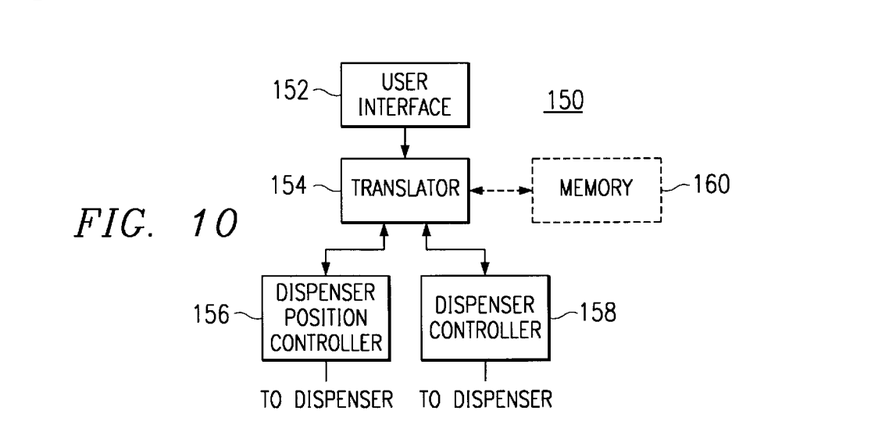
FIG. 10 illustrates one embodiment of an actuating mechanism controller in accordance with the present invention.

User interface 152 has, for example, a push button panel, a selector knob, and/or a control lever to allow a user to input desired instructions to control dispenser 100. Translator 154 receives an indication, whether electrical or mechanical, from user interface 152 and effects the user's instructions via dispenser position controller 156 and dispenser controller 158.

Translator 154 transforms input instructions to effect dispenser 100 movement and/or ligating band 110 dispersal. Depending on whether controller 150 operates mechanically or electro-mechanically, translator 154 may be a central processing unit (CPU), a linear or rotary cam, a linear or rotary shaft, or the like. If translator 154 is a CPU, controller 150 further includes memory 160, which stores programs responsive to user inputs to control the dispenser 100 movement and/or ligating band 110 dispersal. Dispenser position controller 156 and dispenser controller 158 may be pressurized fluid sources, electric motors, solenoids, cams, or the like and are responsive to translator 154 output.

While translator 154 and controllers 156, 158 generally function to move dispenser 100 and cause ligating bands 110 to be dispensed, it is desired that this system further control the actuating forces applied to perform these operations. Application of excessive force could damage dispenser 100 or cause a system malfunction. Accordingly, controller 150 translates user inputs into actuating instructions having prescribed characteristics, for example, actuating distances, applied actuating forces, and/or actuating durations, to prevent damage to dispenser 100 and to ensure systematic and consistent operation of the present invention.

Providing an example of the operation of the present invention, reference will be made to a dispenser 100 having features illustrated in FIGS. 8a, 8c, and 8d, including proximally-biased spring 206 and actuating filaments 200d, 200e.

Dispenser 100 is positioned on the insertion tip 16 of a hosting endoscope 10. Actuating filaments 200 are passed through the work channel of the hosting endoscope 10 and through inlet 28 to the endoscope control portion 12. Actuating filaments 200 are coupled to, for example, controller 150.

For the purpose of this example, dispenser 100 begins in a retracted position. Insertion tip 16 is inserted into a patient, for example, through the mouth, to observe certain internal regions. Dispenser 100 remains in a retracted position during travel of the insertion tip 16 so as to provide the user the broadest field of view detectable by the endoscope image sensing device. Once tissue has been targeted for ligation, the user requests extension of dispenser 100. Controller 150 applies a proximally-directed force to actuating filament 200d for a predetermined time causing dispenser 100 to be extended, thus creating volume 112 defined by the interior surface of sleeve 104. After extension, opening 111 is positioned adjacent to the targeted tissue. The user applies a suction to the appropriate insertion tip 16 outlet, drawing the targeted tissue into volume 112.

The user then requests dispersal of a single ligating band 110a. If ligating band 110a was not loaded by the previous control of actuating filament 200d, controller 150 applies a proximally-directed force to actuating filament 200d for a predetermined duration causing ligating band 100a to be selected. Controller 150 then releases actuating filament 200d to apply a proximally-directed force to actuating filament 200e for a predetermined duration, thus causing ligating band 100a to be dispensed. Upon dispensing a ligating band from dispenser 100, the dispensed ligating band attempts to assume its non-expanded dimensions. As the subject tissue is positioned within an inner diameter of the ligating band, constriction of the band effectively ligates the subject tissue. The applied suction is ceased, and the insertion tip 16 moved away from the ligated tissue. If further exploration is required, actuating filaments 200d, 200e are released and spring 206 biases dispenser 100 again to a retracted position.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A ligating band dispenser, comprising:
   a first member having a surface to support a plurality of ligating bands; and
   a second member, extending at least partially about and being movable relative to the first member, adapted to engage one ligating band of a plurality of ligating bands supported by the surface and continuously move any one engaged ligating band from an initial stored position to a release position.

2. A ligating band dispenser in accordance with claim 1, wherein the second member is adapted to engage and move only a distal-most ligating band supported on the first member for each dispensing cycle.

3. A ligating band dispenser in accordance with claim 2, wherein the second member is adapted to be movably interposed between the distal-most ligating band and the first member and to support the distal-most ligating band from an initial stored position to the release position.

4. A ligating band dispenser in accordance with claim 1, wherein the second member follows a predetermined path parallel to a longitudinal axis of the first member.

5. A ligating band dispenser in accordance with claim 1, wherein the second member follows a predetermined helical path about the first member.

6. A ligating band dispenser, comprising:
a first member having a surface to support a plurality of ligating bands; and
a second member, being movable relative to the first member, having at least one capturing element adapted to engage one ligating band of a plurality of ligating bands supported by the surface and continuously move any one engaged ligating band from an initial stored position to a release position.

7. A ligating band dispenser in accordance with claim 6, wherein the second member is adapted to engage and move only a distal-most ligating band supported on the first member.

8. A ligating band dispenser in accordance with claim 6, wherein the at least one capturing element is adapted to pass over without engaging ligating bands supported by the surface when the second member is moved to a proximal-most position.

9. A ligating band dispenser in accordance with claim 6, wherein the second member follows a predetermined path parallel to a longitudinal axis of the first member.

10. A ligating band dispenser in accordance with claim 6, wherein the second member follows a predetermined helical path about the first member.

11. A ligating band dispenser, comprising:
a first member having a surface to support a plurality of ligating bands; and
a second member, being movable relative to the first member, having at least one capturing element to individually engage and move an engaged ligating band to a release position;
wherein a distance traveled by the second member between a supported, engageable ligating band to a dispensing position increases as each ligating band is dispensed.

12. A ligating band dispenser in accordance with claim 11, wherein an engageable ligating band is a distal-most ligating band supported on the first member.

13. A ligating band dispenser in accordance with claim 11, wherein the distance increases by an amount substantially equal to a band thickness of a single ligating band.

14. A ligating band dispenser, comprising:
a first member having a surface to support at least one ligating band; and
a second member that extends at least partially about the first member and is movable relative to the first member in a direction parallel to a longitudinal axis of the first member, the second member having at least one capturing element to selectively engage and move only a distal-most ligating band supported by the surface.

15. A ligating band dispenser in accordance with claim 14, wherein at least a proximal end of the dispenser is adapted to engage a ligating band dispensing instrument.

16. A ligating band dispenser in accordance with claim 14, wherein at least a proximal end of the dispenser is adapted to engage an insertion portion of a receiving endoscope.

17. A ligating band dispenser in accordance with claim 14, wherein the second member includes a fixed surface and the at least one capturing element includes at least one inwardly-biased member having a contact surface,
wherein a length between the fixed surface and the contact surface of the at least one inwardly-biased member is substantially equal to a band thickness of the distal-most ligating band.

18. A ligating band dispenser in accordance with claim 14, further comprising a member actuating mechanism to control movement of the second member relative to the first member.

19. A ligating dispenser in accordance with claim 14, wherein the dispenser is adapted to move from a retracted position to at least a dispensing position, where at the dispensing position the first member defines a volume by an interior surface thereof sufficient to allow a ligation procedure.

20. A ligating band dispenser in accordance with claim 19, further comprising a dispenser actuating mechanism to control movement of the dispenser from one position to another.

21. A ligating band dispenser in accordance with claim 14, wherein the second member is adapted to follow a predetermined helical path about the first member to effect movement parallel to the longitudinal axis of the first member.

22. A ligating band dispenser, comprising:
a first hollow member adapted to carry at least one expanded ligating band; and
a second hollow member, concentrically arranged with and at least partially surrounding the first member, being movable relative to the first member in a direction parallel to a longitudinal axis of the first member, having at least one inwardly-directed surface to engage and move one ligating band, supported by the surface, in the direction parallel to a longitudinal axis of the first member.

23. A ligating band dispenser in accordance with claim 22, wherein the at least one inwardly-directed surface includes at least one inwardly-biased member.

24. A ligating band dispenser in accordance with claim 23, wherein the at least one inwardly-directed surface includes a fixed shoulder surface,
wherein a distance between the shoulder surface and the inwardly-biased member is substantially equal to a band thickness of the one ligating band.

25. A ligating band dispenser in accordance with claim 22, wherein at least a proximal end of the dispenser is adapted to engage a ligating band dispensing instrument.

26. A ligating band dispenser in accordance with claim 22, wherein at least a proximal end of the dispenser is adapted to engage an insertion portion of a receiving endoscope.

27. A ligating band dispenser in accordance with claim 22, further comprising a first actuating mechanism to control movement of the second member relative to the first member,
wherein the first actuating mechanism effects movement of the second member to engage a ligating band and to dispense an engaged ligating band.

28. A ligating dispenser in accordance with claim 27, wherein the ligating dispenser is movable relative to a carrying instrument, and the first actuating mechanism is adapted to move the dispenser from a retracted position to at least a second position, wherein in the second position, the first member defines a volume by an interior surface thereof sufficient to allow a ligation procedure.

29. A ligating band dispenser in accordance with claim 22, wherein the second member is adapted to follow a predetermined helical path about the first member to effect movement parallel to the longitudinal axis of the first member.

30. A ligating band dispenser in accordance with claim 22, wherein a distance traveled by the second member between a supported, engageable ligating band and a dispensing position increases for each subsequent ligating band dispensed.

31. A ligating band dispenser, comprising:

a first hollow member adapted to carry one or more expanded ligating bands and to be slidably mounted on an insertion portion of a receiving endoscope;

a second hollow member, extending at least partially about the first member and being movable relative to the first member in a direction parallel to a longitudinal axis of the first member, having one or more inwardly-biased members to engage and move a ligating band to a release position for a band dispensing operation; and a first actuating mechanism to selectively move the second member relative to the first member.

32. A ligating band dispenser in accordance with claim 31, further comprising a second actuating mechanism, coupled to the first member, to control movement of the dispenser from a first position to at least a second position.

33. A method for dispensing a ligating band for a ligating band dispenser having a first hollow member, adapted to carry one or more expanded ligating bands, and a second hollow member, at least partially extending about the first member and being movable relative to the first member in a direction parallel to a common longitudinal axis, wherein the second member has one or more inwardly-biased members to engage and move a single ligating band from an original position to a release position, comprising the steps of:

providing the dispenser on an insertion portion of an endoscope;

inserting the insertion portion of the endoscope, including the dispenser, within a patient;

navigating the insertion portion of the endoscope to a desired tissue site;

drawing tissue into a volume defined by the dispenser;

moving the second member proximally until one inwardly-based member is positioned proximate of a distal-most expanded ligating band carried on the first member; and moving the second member distally to move the distal-most expanded ligating band beyond a distal end of the first member to dispense such ligating band.

34. A method in accordance with claim 33, prior to the step of drawing tissue into the volume defined by the dispenser, further comprising the step of extending the dispenser from a retracted position to an extended position relative to the insertion portion, thus forming the volume.

35. A method in accordance with claim 34, further comprising the step of selectively retracting the dispenser.

* * * * *